(12) United States Patent
Mayer

(10) Patent No.: US 8,429,949 B2
(45) Date of Patent: Apr. 30, 2013

(54) CALIBRATION CARD FOR OXYGEN OPTICAL SENSORS

(75) Inventor: Daniel W. Mayer, Wyoming, MN (US)

(73) Assignee: Mocon, Inc., Minneapolis, MN (US)

( * ) Notice: Subject to any disclaimer, the term of this patent is extended or adjusted under 35 U.S.C. 154(b) by 101 days.

(21) Appl. No.: 13/128,040

(22) PCT Filed: Nov. 3, 2009

(86) PCT No.: PCT/US2009/063037
§ 371 (c)(1),
(2), (4) Date: May 6, 2011

(87) PCT Pub. No.: WO2010/053888
PCT Pub. Date: May 14, 2010

(65) Prior Publication Data
US 2011/0209520 A1     Sep. 1, 2011

Related U.S. Application Data

(60) Provisional application No. 61/112,434, filed on Nov. 7, 2008.

(51) Int. Cl.
*G01N 21/00* (2006.01)
(52) U.S. Cl.
USPC .......................................................... 73/1.03
(58) Field of Classification Search ........................ None
See application file for complete search history.

(56) References Cited

U.S. PATENT DOCUMENTS

| 3,612,866 A | 10/1971 | Stevens |
| 4,476,870 A | 10/1984 | Peterson et al. |
| 4,810,655 A | 3/1989 | Khalil et al. |
| 4,947,850 A | 8/1990 | Vanderkooi et al. |
| 5,190,729 A | 3/1993 | Hauenstein et al. |
| 5,371,016 A | 12/1994 | Berndt |
| 5,382,163 A | 1/1995 | Putnam |
| 5,407,829 A | 4/1995 | Wolfbeis et al. |
| 5,483,819 A | 1/1996 | Barmore et al. |
| 5,695,640 A | 12/1997 | Tseng |

(Continued)

FOREIGN PATENT DOCUMENTS

| EP | 0697460 A2 | 2/1996 |
| JP | 2005195354 | 7/2005 |

(Continued)

OTHER PUBLICATIONS

Lee, Sang-Kyung et al., "Photoluminescent Oxygen Sensing on a Specific Surface Area Using Phosphorescence Quenching of Pt-Pophyrin", Analytical Sciences, Department of Bioengineering, Tokyo Institute of Technology, pp. 535-540, Aug. 1997, vol. 13.

(Continued)

*Primary Examiner* — Robert R Raevis
(74) *Attorney, Agent, or Firm* — Sherrill Law Offices, PLLC

(57) ABSTRACT

A calibration card 10 and method of using the card 10 to calibrate an optical sensor. The card 10 comprises (i) a first mass of an oxygen sensitive fluorophore 41 configured and arranged for limiting exposure of the first mass of oxygen sensitive fluorophore 41 to near zero % oxygen, and (ii) a second mass of an oxygen sensitive fluorophore 42 configured and arranged for exposing the second mass of fluorophore 42 to an environmental concentration of oxygen.

22 Claims, 1 Drawing Sheet

U.S. PATENT DOCUMENTS

| | | | |
|---|---|---|---|
| 5,718,842 | A | 2/1998 | Papkovsky et al. |
| 5,837,865 | A | 11/1998 | Vinogradov et al. |
| 6,060,196 | A | 5/2000 | Gordon et al. |
| 6,074,607 | A | 6/2000 | Slovacek et al. |
| 6,153,701 | A | 11/2000 | Potnis et al. |
| 6,165,741 | A | 12/2000 | Wilson et al. |
| 6,171,368 | B1 | 1/2001 | Maget et al. |
| 6,266,211 | B1 | 7/2001 | Thomas, III et al. |
| 6,330,464 | B1 | 12/2001 | Colvin, Jr. et al. |
| 6,362,175 | B1 | 3/2002 | Vinogradov et al. |
| 6,379,969 | B1 | 4/2002 | Mauze et al. |
| 6,395,555 | B1 | 5/2002 | Wilson et al. |
| 6,689,438 | B2 | 2/2004 | Kennedy et al. |
| 6,777,479 | B1 | 8/2004 | Bernard et al. |
| 7,135,342 | B2 | 11/2006 | Colvin, Jr. et al. |
| 7,138,270 | B2 | 11/2006 | Papkovsky et al. |
| 7,248,356 | B2 | 7/2007 | Pfeiffer |
| 7,368,153 | B2 | 5/2008 | Barmore et al. |
| 7,534,615 | B2 | 5/2009 | Havens et al. |
| 7,569,395 | B2 | 8/2009 | Havens et al. |
| 7,740,965 | B2 | 6/2010 | Richards et al. |
| 2002/0164813 | A1 | 11/2002 | Colvin, Jr. et al. |
| 2003/0062262 | A1 | 4/2003 | Mansouri et al. |
| 2005/0159497 | A1 | 7/2005 | Gauthier et al. |
| 2006/0002822 | A1 | 1/2006 | Papkovsky et al. |
| 2006/0144811 | A1 | 7/2006 | Cheng |
| 2007/0041011 | A1 | 2/2007 | Hayden et al. |
| 2007/0212789 | A1 | 9/2007 | Havens et al. |
| 2007/0212792 | A1 | 9/2007 | Havens et al. |
| 2008/0051646 | A1 | 2/2008 | Papkovsky et al. |
| 2008/0117418 | A1 | 5/2008 | Claps et al. |
| 2008/0146460 | A1 | 6/2008 | Pollok et al. |
| 2008/0148817 | A1 | 6/2008 | Miller et al. |
| 2008/0190172 | A1 | 8/2008 | Jones |
| 2008/0199360 | A1 | 8/2008 | Shahriari |
| 2008/0215254 | A1 | 9/2008 | Leiner et al. |
| 2008/0242870 | A1 | 10/2008 | Meador et al. |
| 2009/0028756 | A1 | 1/2009 | Sahahriari |
| 2009/0029402 | A1 | 1/2009 | Papkovsky |
| 2009/0130700 | A1 | 5/2009 | Ince et al. |
| 2011/0084199 | A1* | 4/2011 | Pyo ............................ 250/216 |
| 2011/0154881 | A1 | 6/2011 | Ascheman et al. |
| 2011/0223678 | A1 | 9/2011 | Ascheman et al. |

FOREIGN PATENT DOCUMENTS

| | | |
|---|---|---|
| WO | 9004268 | 4/1990 |
| WO | 9004268 A1 | 4/1990 |
| WO | 2007120637 A2 | 10/2007 |
| WO | 2010053888 A1 | 5/2010 |

OTHER PUBLICATIONS

Eaton, K. et al., "Effect of Humidity on the Response Characteristics of Luminescent PtOEP Thin Film Optical Oxygen Sensors", Sensors & Actuarors B, Elsevier Science B. V., vol. 82, pp. 94-104, 2002.

Technical Manual, "Freudenberg Grafted Products", Sep. 2006, pp. 1-32.

Papkovsky, D. et al., "Phosphorescent Sensor Approach for Non-Destructive Measurements of Oxygen in Packaged Foods: Optimisation of Disposable Oxygen Sensors and Their Characterization Over a Wide Temperature Range", Department of Biochemistry, National University of Ireland, Analytical Letters, 33 (9), pp. 1755-1777, 2000.

De Francisci, M. et al., "Real-Time Estimation of Oxygen Concentration in Micro-Hemo-Vessels", Proceedings of the 26th Annual International Conference of the IEEE EMBS San Francisco, CA, USA' Sep. 1-5, 2004.

* cited by examiner

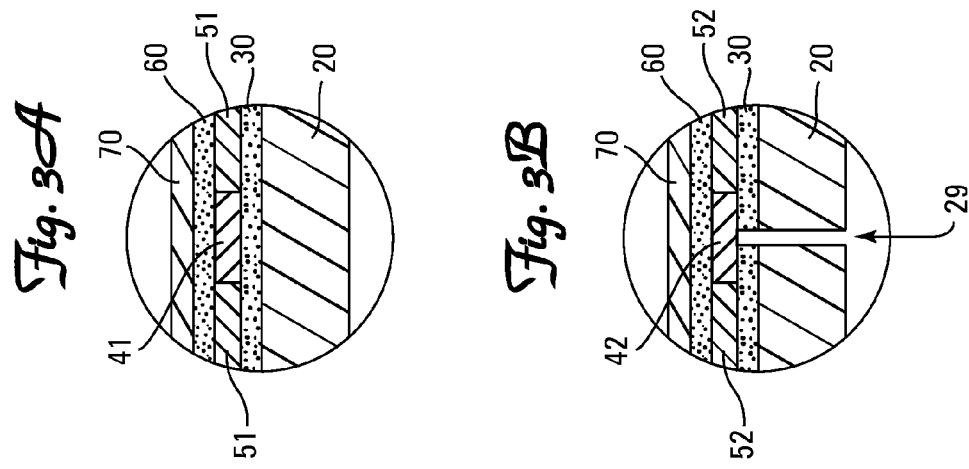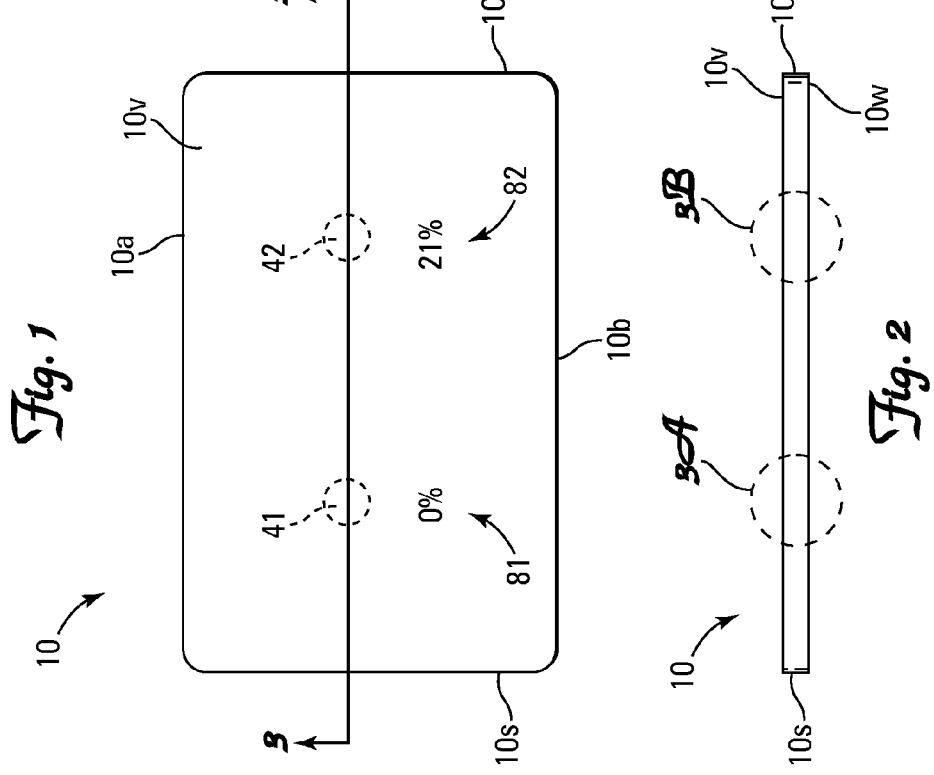

CALIBRATION CARD FOR OXYGEN OPTICAL SENSORS

This application claims the benefit of U.S. Provisional Application No. 61/112,434, filed Nov. 7, 2008.

BACKGROUND

Optical sensors are a widely employed method of measuring analyte concentration, typically oxygen, within a package or container. Briefly, analyte concentration within a package or container can be measured by placing an analyte sensitive fluorophore within the package or container, allowing the fluorophore to equilibrate within the package or container, exciting the fluorophore with radiant energy, and measuring the amount of luminescence emitted by the excite fluorophore. Such optical sensors are available from a number of suppliers, including Presens Precision Sensing, GmbH of Regensburg, Germany.

Such optical sensors are commonly programmed with a calibration mode that permits two-point calibration of the sensor by exposing the analyte sensitive fluorophore to gases having known concentrations of the analyte and sensing luminescence at these known concentrations of analyte (i.e., the fluorophore placed or inserted into a container that has been flushed with certified tank gas containing 0% analyte and luminescence measured, with the fluorophore then placed or inserted into a container that has been flushed with certified tank gas containing 90% analyte and luminescence measured).

While effective for accurately calibrating optical sensors, this calibration method is time consuming and expensive.

Accordingly, a substantial need exists for a low cost system and method for accurately and reliably calibrating an optical sensor.

SUMMARY OF THE INVENTION

A first aspect of the invention is a calibration card for use in calibrating an optical sensor. The calibration card includes at least (i) a first mass of an oxygen sensitive fluorophore isolated from the environment and in fluid communication with an oxygen scavenging material effective for scavenging oxygen from the first mass of fluorophore, and (ii) a second mass of an oxygen sensitive fluorophore in fluid communication with the environment for exposing the second mass of fluorophore to an environmental concentration of oxygen.

A second aspect of the invention is a method of calibrating an optical oxygen sensor having a calibration mode, comprising the steps of: (A) obtaining a calibration card having at least (i) a first mass of an oxygen sensitive fluorophore isolated from the environment and in fluid communication with an oxygen scavenging material effective for scavenging oxygen from the first mass of oxygen sensitive fluorophore, whereby the oxygen concentration to which the a first mass of oxygen sensitive fluorophore is exposed is a known lower value, and (ii) a second mass of an oxygen sensitive fluorophore in fluid communication with the environment for exposing the second mass of oxygen sensitive fluorophore to an environmental concentration of oxygen, whereby the oxygen concentration to which the second mass of oxygen sensitive fluorophore is exposed is a known higher value, (B) setting the optical sensor to calibration mode, and (C) sequentially taking an oxygen concentration reading from each of the masses of oxygen sensitive fluorophore such that the oxygen concentration reading is correlated with the known oxygen concentration to which the mass of oxygen sensitive fluorophore is exposed.

BRIEF DESCRIPTION OF THE DRAWINGS

FIG. 1 is a top view of one embodiment of the invention.

FIG. 2 is a side view of the invention depicted in FIG. 1.

FIG. 3A is an enlarged cross-sectional side view of a portion of the invention shown in FIGS. 1 and 2 taken along line 3-3 and including the 0% oxygen area.

FIG. 3B is an enlarged cross-sectional side view of a portion of the invention shown in FIGS. 1 and 2 taken along line 3-3 and including the 21% oxygen area.

DETAILED DESCRIPTION OF A PREFERRED EMBODIMENT

Definitions

As used herein, including the claims, the phrase "oxygen barrier" means a layer of material that is impervious to oxygen (such as a layer of metal) or significantly impedes the passage of oxygen (such as a plastic film).

As used herein, including the claims, the term "fluorophore" means a molecule with a functional group which can absorb energy of a specific wavelength and as a result emit energy at a different specific wavelength (i.e., a fluorescent molecule).

As used herein, including the claims, the phrase "oxygen sensitive fluorophore" means a fluorophore whose level of fluorescence changes upon exposure to oxygen in proportion to the amount of oxygen.

Nomenclature

10 Calibration Card
10a Top of Calibration Card
10b Bottom of Calibration Card
10r Right Side of Calibration Card
10s Left Side of Calibration Card
10v Upper Major Surface of Calibration Card
10w Lower Major Surface of Calibration Card
20 Support Layer
29 Exposure Channel through Support Layer
30 First Adhesive Layer
40 Mass of Oxygen Sensitive Fluorophore
41 First or 0% Mass of Oxygen Sensitive Fluorophore
42 Second or 21% Mass of Oxygen Sensitive Fluorophore
50 Intermediate Layer
51 Oxygen Scavenging Intermediate Layer
52 Inert Intermediate Layer
60 Second Adhesive Layer
70 Clear Coat or Cover Layer
80 Indicia
81 First Indicia Indicating Mass of Oxygen Sensitive Fluorophore Exposed to 0% Oxygen
82 Second Indicia Indicating Mass of Oxygen Sensitive Fluorophore Exposed to 21% Oxygen

Construction

Referring generally to FIGS. 1 and 2, a first aspect of the invention is a calibration card 10 for use in calibrating an optical oxygen sensor (not shown). The calibration card 10 includes a first mass of oxygen sensitive fluorophore 41 isolated from the environment and in fluid communication with an oxygen scavenging material 51 effective for scavenging oxygen from the first mass 41, and (ii) a second mass of oxygen sensitive fluorophore 52 in fluid communication with the environment for exposing the second mass 52 to an environmental concentration of oxygen.

FIGS. 3A and 3B depict the constructional components of one embodiment of a calibration card 10. As shown in FIGS. 3A and 3B, the calibration card 10 includes laterally spaced first and second masses of oxygen sensitive fluorophore 41 and 42 (collectively referenced as fluorophore masses 40) sandwiched between a support layer 20 and a cover layer 70. The first fluorophore mass 41 is laterally surrounded by an oxygen scavenging portion 51 of an intermediate layer 50. The second fluorophore mass 42 is exposed to the surrounding environment via a channel 29 through the support layer 20 and is laterally surrounded by an inert portion 52 of the intermediate layer 50. Adhesive layers 30 and 60 secure the support layer 20 and the cover layer 70 to the intermediate layer 50 respectively.

The calibration card 10 has a top edge 10a, a bottom edge 10b, a right side edge 10r, a left side edge 10s, an upper major surface 10v and a lower major surface 10w. The card 10 should have a length of about 4 to 20 cm, a width of about 4 to 20 cm, and a thickness of less than 1 cm. A card 10 smaller than this is prone to being lost or misplaced while a card 10 larger than this becomes unnecessarily bulky. The card 10 preferably has a length of about 6 to 10 cm, a width of about 4 to 8 cm, and a thickness of less than 3 mm, and most preferably matches the size of a standard credit card (i.e., about 8.5 cm long, 5.5 cm wide and about 1 mm thick.

The card 10 can be flexible but should also be durable and wear resistant.

The support layer 20 contributes the bulk of the structural integrity to the card 10. The support layer 20 may be transparent, translucent or opaque as desired. The support layer 20 should also function as an oxygen barrier, for reducing the rate at which oxygen permeates through the card 10 and into contact with the oxygen scavenging intermediate layer 51. Suitable materials include specifically, but not exclusively, plastics.

The intermediate layer 50 includes a first portion 51 that laterally surrounds the first fluorophore mass 41 and a second portion 52 that laterally surrounds the second fluorophore mass 42. The first portion 51 of the intermediate layer 50 comprises or includes an oxygen scavenger (not shown) effective for scavenging any oxygen that permeates into the card 10 proximate the first fluorophore mass 41. A wide variety of oxygen scavenging products, including oxygen scavenging films, are known and commercially available. A family of such oxygen scavenging films is available from the Sealed Air division of Cryovac, located in Duncan, S.C. under the designation Cryovac Freshness Plus™ OS films. Two specific oxygen scavenging films suitable for use in the present invention are OS2030 and OS2030AF oxygen scavenging films sold by the Sealed Air division of Cryovac.

The lifespan of the calibration card 10 is dictated by the effective life of the oxygen scavenger employed in the card 10. In order to enhance the lifespan of the card, it is generally preferred to employ oxygen scavengers that can be selectively activated, such as upon exposure to ultraviolet light. The OS2030 and OS2030AF oxygen scavenging films sold by the Sealed Air division of Cryovac are two such films that are selectively activated by ultraviolet light.

The second portion 52 of the intermediate layer 50 is an inert material that may be selected from a wide variety of suitable inert materials, including a wide variety of plastics.

In an alternative embodiment, not shown, the masses of fluorophore 40 may be sandwiched between two intermediate layers 50, which are then laminated onto the support layer 20.

Adhesive layers 30 and 60 may be selected from a wide variety of adhesives suitable for use in laminating plastic layers together, including various hot melt and pressure-sensitive adhesives. It may also be possible to forgo the use of these adhesive layers when the support layer 20, intermediate layer 50 and cover layer 70 are capable of being heat welded together.

Various analyte sensitive fluorophores are known and widely available from a number of sources, including Sigma-Aldrich of St. Louis, Mo. For example, a family of ruthenium-based oxygen sensitive luminescence indicator compositions are disclosed and described in WO 2007/120637. A preferred fluorophore is platinum porphyrin. The benefits of employing platinum porphyrin rather than a ruthenium-based compound as the oxygen sensitive luminescence indicator include (i) less sensitivity to ambient light, (ii) ability to excite at wavelengths other than ultraviolet, (iii) increased sensitivity, and (iv) a longer decay period.

The cover layer 70 provides additional structural integrity to the card 10 and serves as a protective covering for the masses of fluorophore 40 and the intermediate layer 50. The cover layer 70 needs to be transparent or translucent at least at the specific wavelengths at which the masses of fluorophore 40 absorb and emit energy. The cover layer 70 should also function as an oxygen barrier, for reducing the rate at which oxygen permeates through the card 10 and into contact with the oxygen scavenging intermediate layer 51. Suitable materials include specifically, but not exclusively, plastics. Preferred plastics are mylar and polyethylene terephthalate.

The upper major surface 10b of the card 10 is imprinted with first indicia 81 and second indicia 82 (collectively indicia) for identifying the first mass of fluorophore 41 as fluorophore exposed to limited oxygen (e.g., 0%, Zero, Low, Minimum, etc.), and identifying the second mass of fluorophore 42 as fluorophore exposed to an environmental concentration of oxygen (e.g., 21%, Twenty One, High, Maximum, Atmosphere, etc.).

Use

The calibration card 10 can be used to quickly and easily calibrate an optical oxygen sensor (not shown) having a calibration mode. With the calibration card 10, calibration of an optical oxygen sensor (not shown) simply involves the steps of (1) setting the optical sensor to calibration mode, and (2) sequentially taking an oxygen concentration reading from each of the masses of oxygen sensitive fluorophore 41 and 42 such that the oxygen concentration reading is correlated with the known oxygen concentration to which the mass of oxygen sensitive fluorophore 41 or 42 is exposed.

Correlation of the oxygen concentration reading to the oxygen sensitive fluorophore 41 or 42 from which the reading was taken can be accomplished in various ways. One technique is to take the oxygen concentration readings in a predetermined sequence previously input into the optical oxygen sensor (not shown). A second technique is to provide the optical oxygen sensor (not shown) with additional data each time a reading is taken effective for indicating which of the masses of oxygen sensitive fluorophore 41 and 42 was sensed. Yet a third technique is to provide the optical oxygen sensor (not shown) with additional data each time a reading is taken effective for indicating the oxygen concentration to which the sensed mass of oxygen sensitive fluorophore 41 ore and 42 was exposed at the time of the reading.

I claim:

1. A calibration card for use in calibrating an optical sensor, comprising a unitary structure bearing (i) a first mass of an oxygen sensitive fluorophore configured and arranged for limiting exposure of the first mass of oxygen sensitive fluorophore to near zero % oxygen, and (ii) a second mass of an oxygen sensitive fluorophore configured and arranged for exposing the second mass of fluorophore to an environmental concentration of oxygen.

2. The calibration card of claim 1 wherein the first mass of oxygen sensitive fluorophore is isolated from the environment and in fluid communication with an oxygen scavenging material effective for scavenging oxygen from the first mass of fluorophore.

3. The calibration card of claim 1, wherein the card has a length of about 4 to 20 cm, a width of about 4 to 20 cm, and a thickness of less than 1 cm.

4. The calibration card of claim 2, wherein the card has a length of about 6 to 10 cm, a width of about 4 to 8 cm, and a thickness of less than 3 mm.

5. The calibration card of claims 1 or 2, wherein the fluorophore in both the first and second masses of fluorophore are the same.

6. The calibration card of claims 1 or 2, wherein the first and second masses of fluorophore are sandwiched between an oxygen barrier support layer and an oxygen barrier transparent cover layer.

7. The calibration card of claim 6, wherein the transparent cover layer is a transparent layer of polyethylene terephthalate.

8. The calibration card of claim 2, wherein the oxygen scavenging material is activated by exposure to ultraviolet light.

9. The calibration card of claim 8, wherein the oxygen scavenging material is incorporated into a film.

10. The calibration card of claims 1 or 2, wherein the card contains first indicia tagging the first mass of fluorophore as fluorophore exposed to limited oxygen, and second indicia tagging the second mass of fluorophore as fluorophore exposed to an environmental concentration of oxygen.

11. The calibration card of claim 10, wherein the first indicia comprises at least the designation 0% and the second indicia comprises at least the designation 21%.

12. The calibration card of claim 6, wherein the second mass of fluorophore is in fluid communication with the environment via at least one channel through the support layer.

13. A method of calibrating an optical oxygen sensor having a calibration mode, comprising the steps of: (A) obtaining a calibration card having at least (i) a first mass of an oxygen sensitive fluorophore configured and arranged for limiting exposure of the first mass of oxygen sensitive fluorophore to oxygen, whereby the oxygen concentration to which the first mass of oxygen sensitive fluorophore is exposed is a known lower value, and (ii) a second mass of an oxygen sensitive fluorophore in fluid communication with the environment for exposing the second mass of oxygen sensitive fluorophore to an environmental concentration of oxygen, whereby the oxygen concentration to which the second mass of oxygen sensitive fluorophore is exposed is a known higher value, (B) setting the optical sensor to calibration mode, and (C) sequentially taking an oxygen concentration reading from each of the masses of oxygen sensitive fluorophore such that the oxygen concentration readings are correlated with the lower and higher values to which the mass of oxygen sensitive fluorophore is exposed.

14. A method of calibrating an optical oxygen sensor having a calibration mode, comprising the steps of: (A) obtaining a calibration card having at least (i) a first mass of an oxygen sensitive fluorophore isolated from the environment and in fluid communication with an oxygen scavenging material effective for scavenging oxygen from the first mass of oxygen sensitive fluorophore, whereby the oxygen concentration to which the first mass of oxygen sensitive fluorophore is exposed is a known lower value, and (ii) a second mass of an oxygen sensitive fluorophore in fluid communication with the environment for exposing the second mass of oxygen sensitive fluorophore to an environmental concentration of oxygen, whereby the oxygen concentration to which the second mass of oxygen sensitive fluorophore is exposed is a known higher value, (B) setting the optical sensor to calibration mode, and (C) sequentially taking an oxygen concentration reading from each of the masses of oxygen sensitive fluorophore such that the oxygen concentration readings are correlated with the lower and high values to which the mass of oxygen sensitive fluorophore is exposed.

15. The method of claims 13 or 14, where step (C) comprises at least the step of taking an oxygen concentration reading from each of the masses of oxygen sensitive fluorophore in a predetermined sequence.

16. The method of claims 13 or 14, wherein step (C) comprises at least the steps of: (1) sensing the oxygen concentration to which one of the masses of oxygen sensitive fluorophore is exposed using the optical sensor in calibration mode, (2) providing the optical sensor with data indicating which of the masses of oxygen sensitive fluorophore on the calibration card was sensed, and (3) sensing the oxygen concentration to which the other mass of oxygen sensitive fluorophore is exposed using the optical sensor in calibration mode.

17. The method of claims 13 or 14, wherein step (C) comprises at least the steps of: (1) sensing the oxygen concentration to which one of the masses of oxygen sensitive fluorophore is exposed using the optical sensor in calibration mode, (2) providing the optical sensor with data indicating the known oxygen concentration to which the one mass of oxygen sensitive fluorophore is exposed, (3) sensing the oxygen concentration to which the other mass of oxygen sensitive fluorophore is exposed using the optical sensor in calibration mode, and (4) providing the optical sensor with data indicating the known oxygen concentration to which the other mass of oxygen sensitive fluorophore is exposed.

18. The method of claim 13, wherein the card has a length of about 6 to 10 cm, a width of about 4 to 8 cm, and a thickness of less than 3 mm.

19. The method of claims 13 or 14, wherein the first and second masses of oxygen sensitive fluorophore are sandwiched between an oxygen barrier support layer and an oxygen barrier transparent cover layer.

20. The method of claim 14, wherein the oxygen scavenging material is activated by exposure to ultraviolet light prior to taking an oxygen concentration reading from the masses of oxygen sensitive fluorophore.

21. The method of claims 13 or 14, wherein the card contains first indicia tagging the first mass of oxygen sensitive fluorophore as the mass exposed to no oxygen, and second indicia tagging the second mass of oxygen sensitive fluorophore as the mass exposed to an environmental concentration of oxygen.

22. The method of claim 21 wherein the first indicia comprises at least the numerical value 0% and the second indicia comprises at least the numerical value 21%.

* * * * *